US010566084B2

(12) United States Patent
Kataoka

(10) Patent No.: US 10,566,084 B2
(45) Date of Patent: Feb. 18, 2020

(54) SYSTEM AND METHOD FOR RACING DATA ANALYSIS USING TELEMETRY DATA AND WEARABLE SENSOR DATA

(71) Applicant: NTT Innovation Institute, Inc., Palo Alto, CA (US)

(72) Inventor: Yasuyuki Kataoka, Palo Alto, CA (US)

(73) Assignee: NTT Innovation Institute, Inc., Palo Alto, CA (US)

( * ) Notice: Subject to any disclaimer, the term of this patent is extended or adjusted under 35 U.S.C. 154(b) by 0 days.

(21) Appl. No.: 16/109,548

(22) Filed: Aug. 22, 2018

(65) Prior Publication Data

US 2019/0156934 A1    May 23, 2019

Related U.S. Application Data

(60) Provisional application No. 62/549,415, filed on Aug. 23, 2017.

(51) Int. Cl.
| | |
|---|---|
| *G16H 20/30* | (2018.01) |
| *G06N 20/00* | (2019.01) |
| *A61B 5/11* | (2006.01) |
| *A63K 99/00* | (2006.01) |
| *G06K 9/62* | (2006.01) |
| *G07C 5/02* | (2006.01) |

(52) U.S. Cl.
CPC ............ *G16H 20/30* (2018.01); *A61B 5/1118* (2013.01); *A63K 99/00* (2013.01); *G06K 9/6218* (2013.01); *G06N 20/00* (2019.01); *G07C 5/02* (2013.01)

(58) Field of Classification Search
CPC ...... G16H 20/30; G06N 20/00; A61B 5/1118; A63K 99/00; G06K 9/6218; G07C 5/02
USPC .......................................................... 700/91
See application file for complete search history.

(56) References Cited

U.S. PATENT DOCUMENTS

| | | | |
|---|---|---|---|
| 6,575,902 B1 * | 6/2003 | Burton ................. | A61B 5/18 600/300 |
| 9,144,389 B2 * | 9/2015 | Srinivasan .......... | A61B 5/0408 |
| 9,674,880 B1 * | 6/2017 | Egner ................. | H04W 4/029 |
| 2009/0066521 A1 * | 3/2009 | Atlas ................... | A61B 5/18 340/575 |
| 2010/0286572 A1 * | 11/2010 | Moersdorf ........... | A61B 5/0002 600/595 |

OTHER PUBLICATIONS

Kegelman, J.C., et al., entitled "Insights into vehicle trajectories at the handling limits: analysing open data from race car drivers; Taylor & Francis, Vehicle System Dynamics" dated Nov. 3, 2016 (18 pgs.).

(Continued)

*Primary Examiner* — Allen Chan
(74) *Attorney, Agent, or Firm* — DLA Piper LLP (US)

(57) ABSTRACT

A system and method for racing data analysis using telemetry data and wearable sensor data may be used, in one implementation, to analyze muscle use in extreme racing conditions to find actionable insights for the race car driver. An example of the actionable insights may be how to minimize the driver's muscle fatigue during a race. The system and method may perform data validation of the data from the wearable sensor(s) and then generate the actionable insights from the validated data.

17 Claims, 12 Drawing Sheets

(56) References Cited

OTHER PUBLICATIONS

Theodosis, P. et al., entitled "Nonlinear Optimization of a Racing Line for an Autonomous Racecar Using Professional Driving Techniques" Abstract Only, retrieved from the web at https://www.researchgate.net/publication/267650184_Nonlinear_Optimization_of_a_Racing_Line_for_an_Autonomous_Racecar_Using_Professional_Driving_Techniques_dated_October_2012 (3pgs).
Tulabandhula, T. et al. "Tire Changes, Fresh Air, and Yellow Flags: Challenges in Predictive Analytics for Professional Racing" MIT, dated Jun. 2014 (16 pgs.).
Takagahara,. K. et al.: "hitoe"—A Wearable Sensor Developed through Cross-industrial Collaboration, NTT Technical Review, dated Sep. 4, 2014 (5 pgs.).
Lee, J.H., et al., Development of a novel Tympanic temperature monitoring system for GT car racing athletes—Abstract Only—retrieved from the web at https://link.springer.com/chapter/10.1007/978-3-642-29305-4_541 pp. 2062-2065, dated 2013 (3 pgs.).
Kataoka et al, "Mining Muscle Use Data for Fatigue Reduction in IndyCar," MIT Sloan Sports Analytics Conference (Mar. 4, 2017), pp. 1-12. Retrieved from the Internet. <URL: http://www.sloansportsconference.com/wp-content/uploads/2017/02/1622.pdf>.

\* cited by examiner

SYSTEM AND METHOD FOR RACING DATA ANALYSIS USING TELEMETRY DATA AND WEARABLE SENSOR DATA

PRIORITY CLAIMS/RELATED APPLICATIONS

This application claims the benefit under 35 USC 119(e) to U.S. Provisional Patent Application Ser. No. 62/549,415, filed Aug. 23, 2017 and entitled "System And Method For Racing Data Analysis Using Telemetry Data And Wearable", the entirety of which is incorporated herein by reference.

FIELD

The disclosure relates generally to vehicle insights and in particular to fatigue reduction insights for a racing car.

BACKGROUND

Car racing takes a toll on the body of a driver. For example, IndyCar is an American-based auto racing sanctioning body for Championship auto racing. Unlike other racing formats, such as the Formula One, IndyCar has regulations forbidding the use of power steering. This requires drivers to exert force with their forearms when turning the wheel, which dramatically deteriorates the driver's performance as the forearm muscles become fatigued during a race. Hence, saving a driver's muscle use during a race is a beneficial insight for the driver. Thus, it is desirable to be able to solve the problem of driver muscle fatigue and thus improve driving performance.

In the research of auto-racing, various approaches are conventionally taken to improve driver's performance or safety. One approach is the trajectory path optimization based on the driver's record. Kegelman, J. C., Harbott, L. K., & Gerdes, J. C. (2016). Insights into vehicle trajectories at the handling limits: Analyzing open data from race car drivers. *Vehicle System Dynamics*. The findings from trajectory analysis are used for the path planning of self-driving cars. Theodosis, P. A., & Gerdes, C. J. (2012). Nonlinear Optimization of a Racing Line for an Autonomous Racecar Using Professional Driving Techniques. *ASME 2012 5th Annual Dynamic Systems and Control Conference joint with the JSME 2012 11th Motion and Vibration Conference*. Another approach is a real-time decision system for tire changes within a race. Tulabandhula Theja and Rudin Cynthia (2014). Tire Changes, Fresh Air, and Yellow Flags: Challenges in Predictive Analytics for Professional Racing. *Big Data*. Moreover, there is research for driver's safety. One approach is around heat prevention using a temperature sensor on the driver.[4] Lee, J. H., Matsumura, K., Yamakoshi, K., Rolfe, P., Tanaka, N., Yamakoshi, Y., . . . Yamakoshi, T. (2013). Development of a novel Tympanic temperature monitoring system for GT car racing athletes. In *World Congress on Medical Physics and Biomedical Engineering*.

However, no publicly available papers or systems focused on analyzing forearm use during a race with the consideration of heterogeneous data. Thus, it is desirable to provide a technical solution to this problem as disclosed below.

DETAILED DESCRIPTION OF ONE OR MORE EMBODIMENTS

Figure 1:
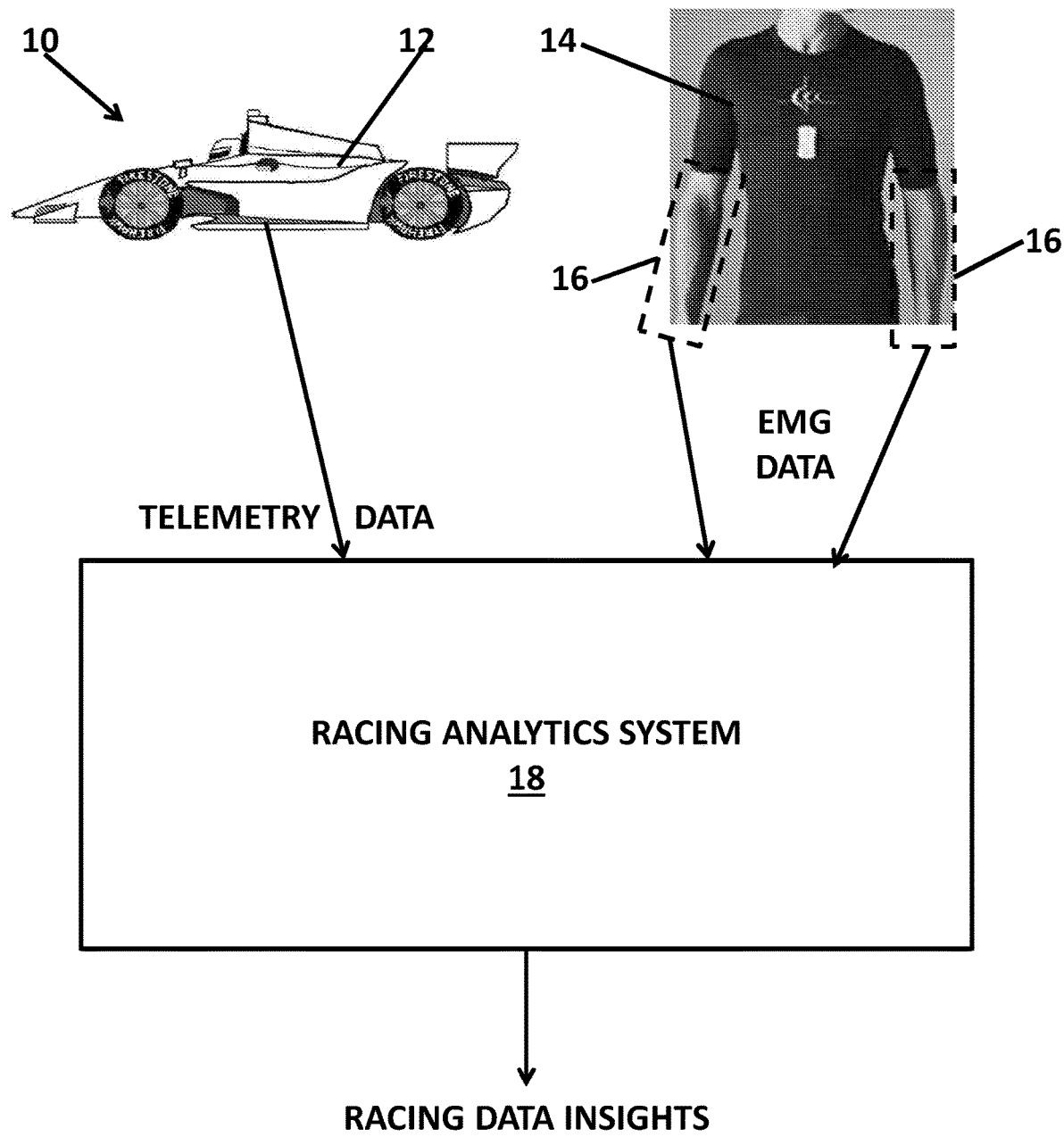
FIG. 1 illustrates an example of an implementation of a vehicle data analytics system that may be used for providing insights for forearm muscle fatigue.

The disclosure is particularly applicable to forearm fatigue insights for racing vehicles that do not permit power steering and it is in this context that the disclosure will be described. It will be appreciated, however, that the system and method has greater utility since it may be used to determine insights for other factors to improve driver performance, it may be used for other types of vehicles and may be implemented in other ways than those disclosed below in the disclosed embodiments.

The system and method may solve the above problem of assessing driver performance and driver fatigue using one or more wearable sensors, telemetry data from the vehicle and a racing data analysis system that uses the data from the one or more wearable sensors and the telemetry data from the vehicle to generate actionable insights to improve driver performance. In one embodiment, the system and method may generate actionable insights about how to reduce forearm muscle fatigue in race cars without power steering wherein the actionable insights may be, for example, locations on a race circuit at which the driver may relax his forearm muscles and reduce the fatigue.

In the exemplary embodiment for improving the driver's performance with the focus on muscle use and fatigue, the system and method tackles two major technological challenges including: 1) data validation on noisy signal obtained from wearable sensors in extreme condition as might exist in a race car; and 2) data cultivation to find actionable insights for the driver from heterogeneous racing data.

One of the common challenges for wearable devices is data quality and validation. The quality of the signal coming from wearable device is very sensitive to whether or not it is properly attached to the body. Thus, the system and method may use a data quality validation technique that enables the judgment of whether the data is reliable or not. This methodology is based on the comparison between actual Electromyogram (EMG) data and predicted EMG data, which is computed by a Machine Learning technique as described below. If the actual EMG deviates significantly from the predicted EMG, the actual EMG is considered not to be valid. To guarantee the performance of the prediction, the feature in the prediction model uses only the car's telemetry information, i.e., excluding the EMG information itself, as a feature since the EMG signal itself may be too noisy to use for prediction, while the car's telemetry information can provide stable signals. In one embodiment, test data shows that this qualitative analysis based data validation method works with 99.5% accuracy to classify the data reliability.

For data cultivation to find actionable insights, the system and method provide a data visualization and interaction engine that enables the race team to cultivate heterogeneous data and discover useful insights in an intuitive manner. The computation method behind this engine may be, in one implementation, a multi-modal analysis of EMG and car telemetry data. The analysis may be unsupervised learning using the following technique: 1. cluster data points in a geographical fashion; and 2. find similarity between EMG and the car's telemetry data. Based on this analysis, locations are identified where the driver exerts unnecessary force during the race, in other words, where the driver may be able to rest and recover as shown for example in FIG. 15

FIG. 1 illustrates an example of an implementation of a vehicle data analytics system 10 that may be used for providing insights for forearm muscle fatigue. The system may generally receive data about the vehicle and data about the driver and generate, using machine learning in part, driving performance insights. In one exemplary implementation described herein, the system and method may receive/obtain vehicle telemetry data, data from the muscles of one or more forearms of a driver of the vehicle and generate insights about how the driver may reduce muscle fatigue of the forearms while driving the vehicle that does not have power steering. The system 10 may include a vehicle 12, such as an Indycar racing car for example, from which various car telemetry data, such as for example accelerometer data (latitude, longitude, vertical), steering angle, speed (mph), throttle pressure, brake pressure, engine rpm, angular acceleration, etc. may be obtained and communicated to a racing analytics system 18. The system 10 may also have a driver garment 14 having one or more wearable sensors 16, such as for example electromyogram (EMG) sensors on each forearm in the implementation for forearm muscle fatigue, wherein the data from the one or more wearable sensors may be communicated to the racing analytics system 18. The racing analytics system 18 may receive the telemetry data and sensor data, perform the data validation on noisy signal obtained from wearable sensors in extreme condition as might exist in a race car and perform the data cultivation to find actionable insights for the driver from heterogeneous racing data. In the forearm muscle fatigue example discussed below, the system may generate, for example, locations on the race circuit at which the driver may be able to relax his forearms and thus reduce the fatigue of the forearm muscles.

Figure 2:
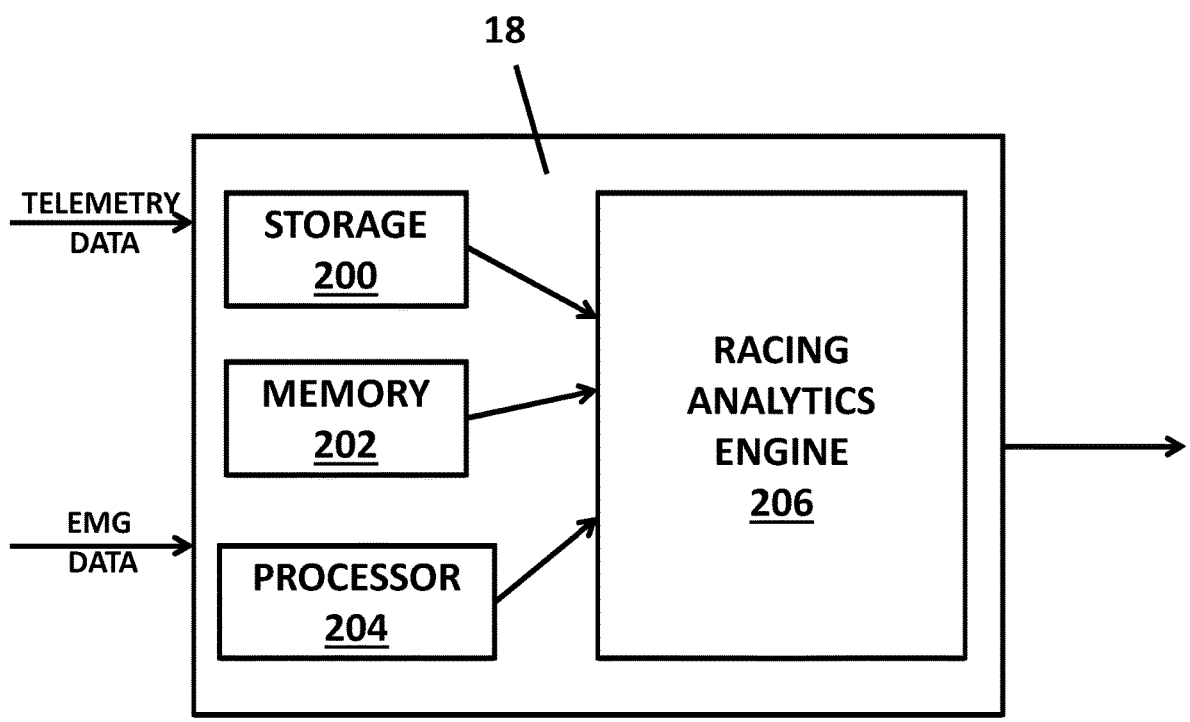
FIG. 2 illustrates more details of the vehicle data analytics system.

FIG. 2 illustrates more details of the vehicle data analytics system 18. The vehicle data analytics system 18 may be implemented in hardware or software. When the vehicle data analytics system 18 is implemented in hardware, each element of the racing analytics engine 206 (shown in more detail in FIG. 3) may be a hardware device that is specialized to perform the analysis and data validation as described below. Alternatively, one or more elements of the racing analytics engine 206 may be implemented using the same hardware device. When the vehicle data analytics system 18 is implemented in software (an example of which is shown in FIG. 2), a racing analytics engine 206 and each element of the racing analytics engine 206 (shown in FIG. 3) may be implemented using a plurality of lines of instructions/computer code that may be executed by a processor of a computer system that hosts the racing analytics engine 206 so that the processor of the computer system is configured to perform the operations and processes of each of the elements of the racing analytics engine 206. The computer system that hosts the elements of the racing analytics engine 206 in a software implementation may be one or more server computers, one or more application servers, one or more cloud computing resources and the like. In one example, the computer system may include storage 200, memory 202 and one or more processors 204. The storage 200 may be a software or hardware implemented storage mechanism that may store, for example, telemetry data, the EMG data, user data, the computer code used to perform the operations and processes of the each of the elements of the racing analytics engine 206 and the results of the data analytics process as described below. The memory 202 may temporarily store the telemetry and EMG data, may store the code being executed by the processor to perform the operations and processes of the each of the elements of the racing analytics engine 206 and may store the results of the data analytics. The processor 204 may execute the code/plurality of instructions so that the computer system is configured to perform the operations and processes of the each of the elements of the racing analytics engine 206. As shown in FIG. 2, the vehicle data analytics system 18 may receive the telemetry data and the sensor data, such as EMG data for the forearm fatigue example use case, and may generate one or more driver performance insights based on a combination of the telemetry data and the sensor data to improve the performance of the driver. In the forearm fatigue example use case, the one or more driver performance insights may be one or more locations on a racing circuit (a route over which the vehicle is racing that may be a track, a speedway or streets/roads) at which the driver may be able to relax the forearm muscles. For example, the insights may indicate that a straight portion of the racing circuit should be a location on the racing circuit during which the driver should be relaxing his forearm muscles.

Figure 3:
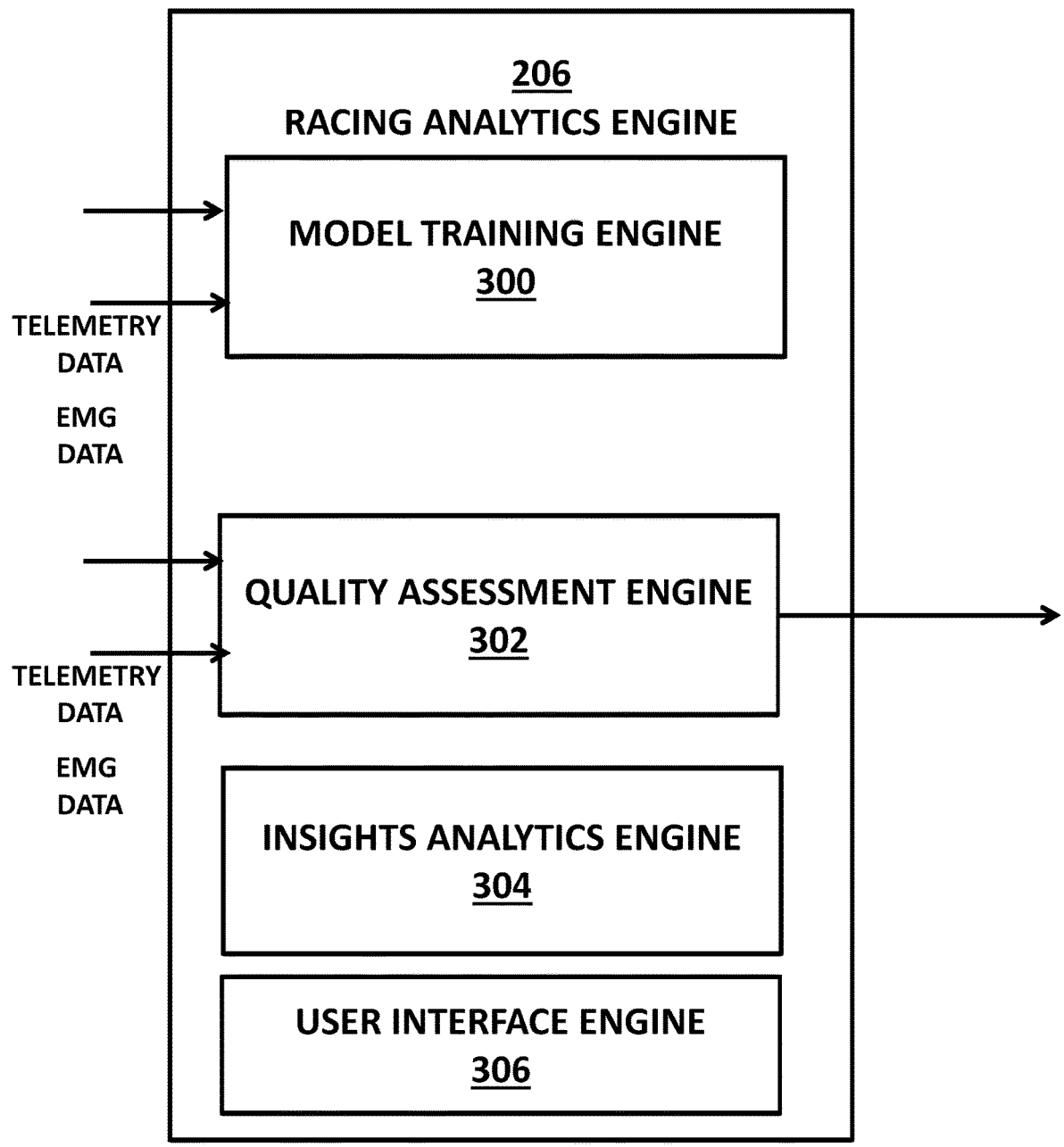
FIG. 3 illustrates more details of the racing analytics engine of the vehicle data analytics system.

FIG. 3 illustrates more details of the racing analytics engine 206 of the vehicle data analytics system. The racing analytics engine 206 may include a model training engine 300 and quality assessment engine 302 that may together perform the wearable sensor validation process and thus, for example, determine if the received wearable sensor data is valid and usable to generate the insights of the system. The model training engine 300 may implement a machine learning process (shown in more detail in FIG. 6) that trains a machine learning model so that the machine learning model may be used to validate the wearable sensor data and determine if the wearable sensor data is valid and thus usable during the insight analytics process. The quality assessment engine 302 uses the trained model (trained by the model training engine 300) to generate predictions (using machine learning techniques) to validate each piece of wearable sensor data. In one embodiment, the quality assessment engine 302 may compare the predicted sensor value by the trained model against the actual sensor data to validate each piece of wearable sensor data since the sensor data is noisy as described above. The model training engine 300 and the quality assessment engine 302 provide a technical solution and improvement to the process of driver improvement data and solve the problem of noisy sensor data described above.

The racing analytics engine 206 may further include an insight analytics engine 304 that receives the telemetry data, the validated sensor data and GPS data to generate the one or more insights. In one embodiment, this engine 304 may perform clustering and similarity analysis to generate the one or more insights. In the forearm fatigue example, this engine may generate insights for locations on the race circuit at which the drive should relax his forearm muscles. The insight analytics engine 304 provides a technical solution and improvement to the process of generating driver insights and solves the problem of being able to automatously generate the driver performance insights.

The racing analytics engine 206 may further include a user interface engine 306 that may generate the visual displays of the processes, such as reports, data visualizations of the actionable insights and the like as shown in FIGS. 10-15.

Data Collection

Before the insights are generated or contemporaneously when the insights are being generated, a variety of data points may be collected while the driver is on the race circuit. In one embodiment, the one or more wearable sensors may include electrocardiogram (ECG) sensors located around the rib cage and one or more sensors that collect signals for EMG with sensors located around the forearm. The sensors communicate through a bluetooth receiver connected to an onboard telemetry system of the vehicle and are at some point communicated to the system 18. The bluetooth receiver may capture data at 200 samples per second and each race offers different number of laps ranging between 50 to 300 laps with an average distance of 2.2 miles per lap.

In addition to the driver's wearable sensor information, the method may collect from the onboard telemetry system of the vehicle, telemetry data including accelerometer data (latitude, longitude, vertical), steering angle, speed (mph), throttle pressure, brake pressure, engine rpm, and/or angular acceleration. The system 10 may also gather GPS coordinates (relative to a fixed point on the track), and seconds of gap between the car ahead and behind the driver.

The data above may be collected through a private network that is accessible during the race allowing the team to do near-real time analysis although the system 10 may also perform post-race analysis with the data that may be downloaded from the vehicle's telemetry system after the race. The system may also collect timestamps from the real time clock (RTC) onboard the vehicle. The RTC is used to anchor data collected across differing frequencies. Using this RTC channel value, data from all channels is realigned to the highest frequency channel, while listing a blank value where the source channel collected data at a lower frequency.

In one embodiment, the wearable garment may be a hitoe wearable sensor developed by NTT Docomo that is described in an article by Kazuhiko Takagahara et al. ""hitoe"—A Wearable Sensor Developed through Cross-industrial Collaboration" that may be found at https://www.ntt-review.jp/archive/ntttechnical.php?contents=ntr201409ra1.html which is incorporated herein by reference. This hitoe wearable sensor technology may include the one or more EMG sensors to generate the EMG data since each EMG sensor is known and commercially available.

Validation of Sensor Data Process

To solve the technical problem of the noisy wearable sensor data as described above, the system may perform validation of the wearable sensor data to determine if the wearable sensor data can be used for generating the one or more insights generated by the system. In one embodiment, the data validation process may be performed by the model training engine 300 and the quality assessment engine 302 shown in FIG. 3.

The data validation process for vehicle racing is particularly important since the quality of the signal coming from wearable devices are very sensitive to whether the sensor is properly attached to the body or not. In the case of IndyCar racing, the sensor data is highly affected by the extreme forces experienced in racing conditions. If the data is not valid and reliable, it may lead to faulty analysis and incorrect insights.

Figure 4:
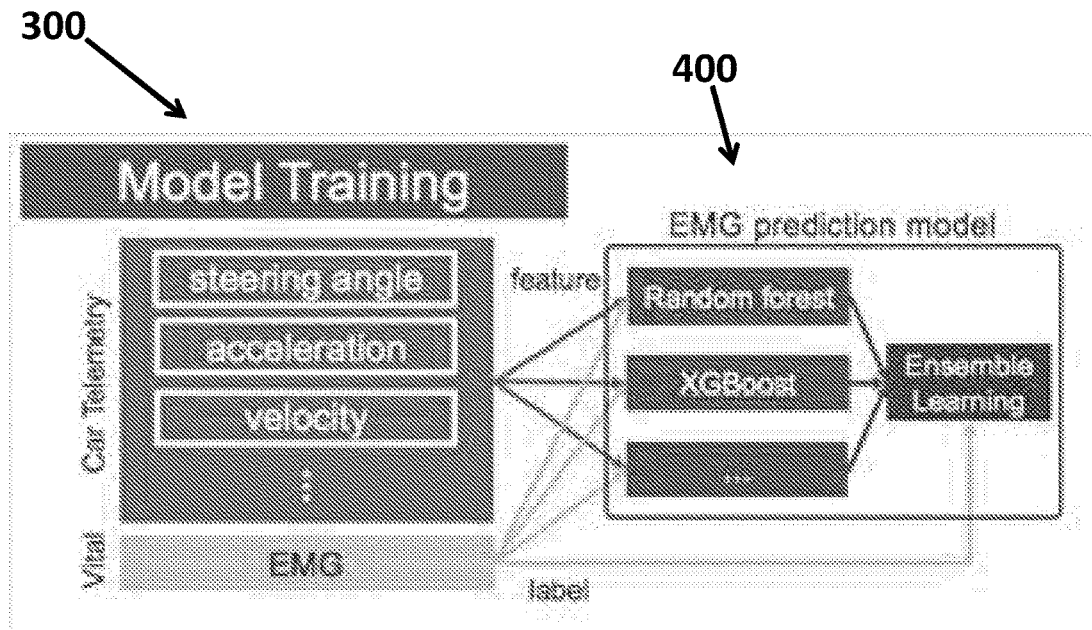
FIG. 4 illustrates an example of an implementation of the model training engine of the racing analytics engine.
Figure 5:
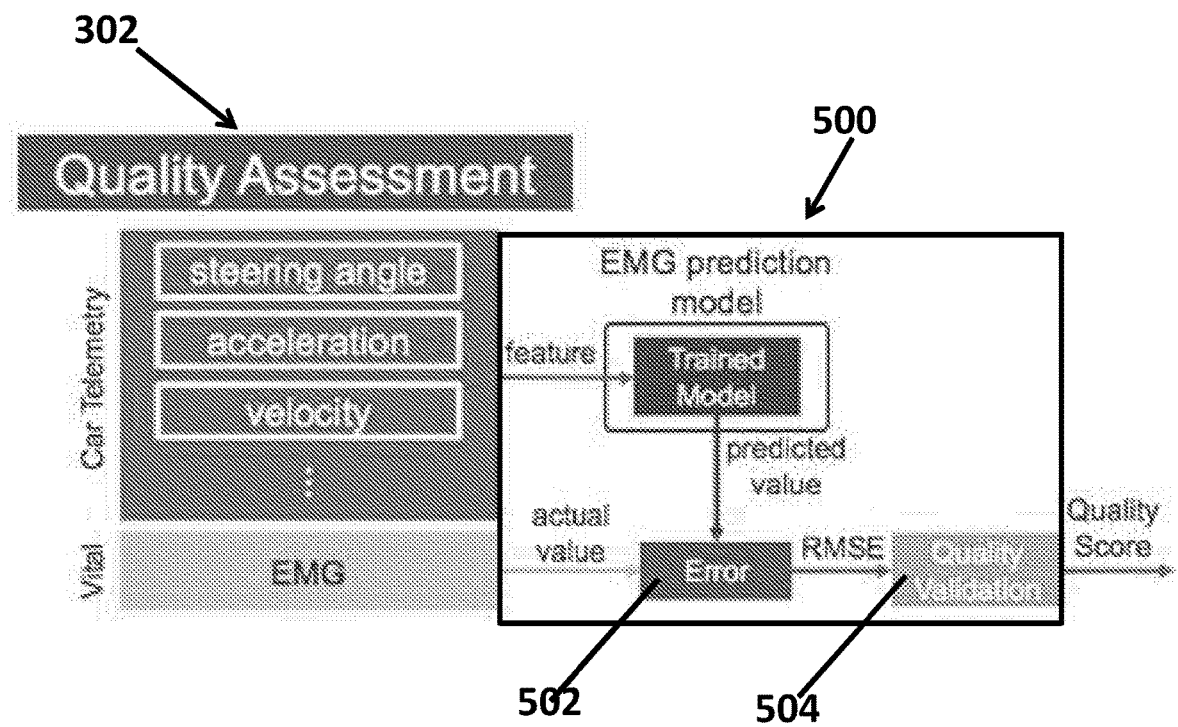
FIG. 5 illustrates an example of an implementation of the quality assessment engine of the racing analytics engine.

The methodology for data validation is based on the comparison of actual EMG data and predicted EMG as shown in FIG. 5 and performed by the quality assessment engine 302. If the driver's actual EMG significantly deviates from the predicted EMG, the collected EMG is not considered valid (as indicated by the generated quality score). The methodology relies on predicting the EMG value with high accuracy in a reliable manner via Machine Learning using the model training engine 300 shown in FIG. 4. In the model that is trained, the system and method use only heterogeneous and reliable car telemetry data as features for the prediction model, i.e., excluding the collected EMG information as a feature. In some embodiments, the data validation may be performed for each lap of the race course since further analysis depends on lap data.

Machine Learning Model Training Process

Part of the data validation process is the training of a machine learning model that may then be used to assess the quality of the wearable sensor data. FIG. 4 illustrates an example of an implementation of the model training engine 300 of the racing analytics engine. The model training engine 300 may train an EMG data prediction model 400. The data set may include: [3-axis acceleration respectively [m/s^2], throttle pedal[%], gyro[rad/s], lap number, pressure brake, speed, steering, hitoe EMG.

In an embodiment shown in FIG. 4, the model 400 may be trained via machine learning. As explained above, the data and features used for the training may be the various telemetry data. In one implementation, the machine learning may use ensemble learning that aggregates different prediction algorithms such as Random Forest, XGBoost, etc. This way, the model 400 can leverage diverse prediction models to produce more accurate results. The ensemble learning is one example of the process by which the model may be trained.

The features for the machine learning are simply designed by car telemetry data. The EMG data is not used as a feature since it is highly affected by how the wearable device is attached to body as described above. In the extreme conditions of IndyCar, temporary detachment from the driver's body can easily happen. Thus, to create the EMG prediction model, the process only leverages reliable and heterogeneous data (e.g., the telemetry data). The model training process may use clean labeled EMG data and method may use datasets obtained from firmly attached wearable fabric (less noisy data) for this training phase.

Quality Assessment Process

Figure 16:
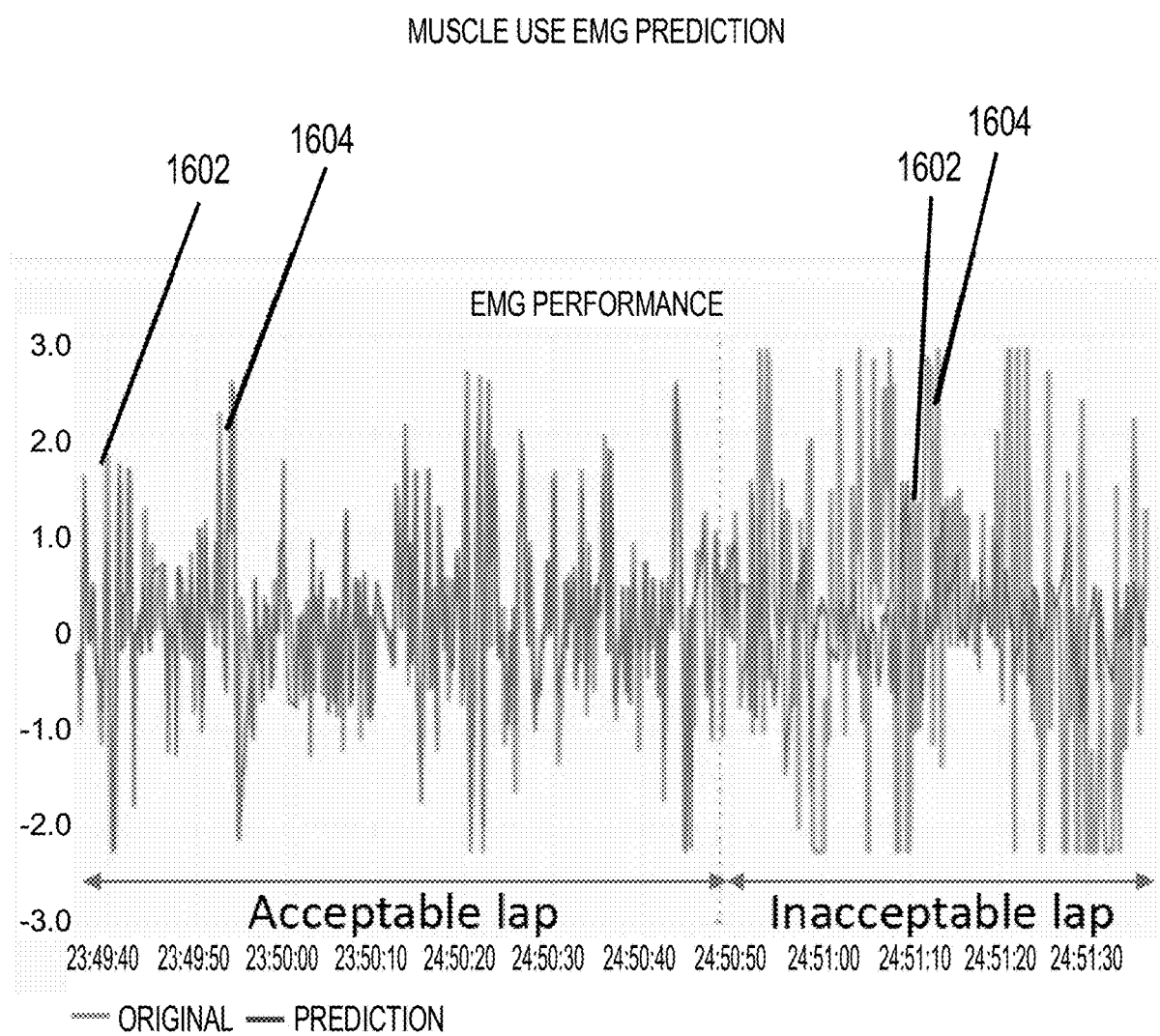
FIG. 16 illustrates an example of the EMG data quality assessment process.

As a second part of the data validation process, the quality of each piece of wearable sensor data, such as EMG data in one example, is assessed. FIG. 5 illustrates an example of an implementation of the quality assessment engine 302 of the racing analytics engine that may be used to perform the quality assessment. During this process, the quality of the wearable sensor data is measured and judged whether it is usable for further analysis. The data quality assessment process 500 is based on the error between actual EMG values and predicted EMG values. In some embodiments, the system and method may validate data quality lap by lap for the next level of analysis as shown in FIG. 16.

In the process 500, wearable sensor data may be predicted using the features of the telemetry data and the model trained during the model training process 400. Again, the features for this model are only composed of car telemetry information which provide stable signals. Thus, these predicted EMG values are assumed to be able to be acceptably accurate. Thus, as shown in FIG. 16, a first line 1602 (a green line in a color drawing) shows the original EMG value coming from sensor and a second line 1604 (shown in red in a color drawing) shows the predicted value from EMG using only car telemetry data. As shown in FIG. 16, if the green line 1602 and red line 1604 correspond closely each other (left side of the figure), they are clean data (acceptable lap), but if the two lines 1602, 1604 does not correspond to each other (right side of the figure), then the EMG data is not acceptable since the quality of the sensor measured EMG data is too different from the predicted values.

The process 500 may then perform an error determination process 502 in which the error between the predicted wearable sensor data and the actual wearable sensor data is determined. In one implementation, the error may be computed using the following algorithm/formula:

$$e_l = \frac{\sum_{k=0}^{N_l} \sqrt{(y_k^{[p]} - y_k^{[a]})^2}}{N_l} \quad (1)$$

where l represents the lap index, $e_l$ represents the average error (RMSE: Root Mean Squared Error) in lap l, $N_l$ represents the number of data point of EMG in lap l, $y_k^{(p)}$ represents the predicted EMG at data index=k, and $y_k^{(a)}$ represents the actual EMG at index k. Thus, the result of the error determination is an average error value. The process 500 may then have a quality validation process 504 that determined if the data at lap l can be used for advanced analytics or not. This classification is based on threshold against $e_l$. This threshold is experimentally setup, which performs the best classification performance on training data.

Figure 6:
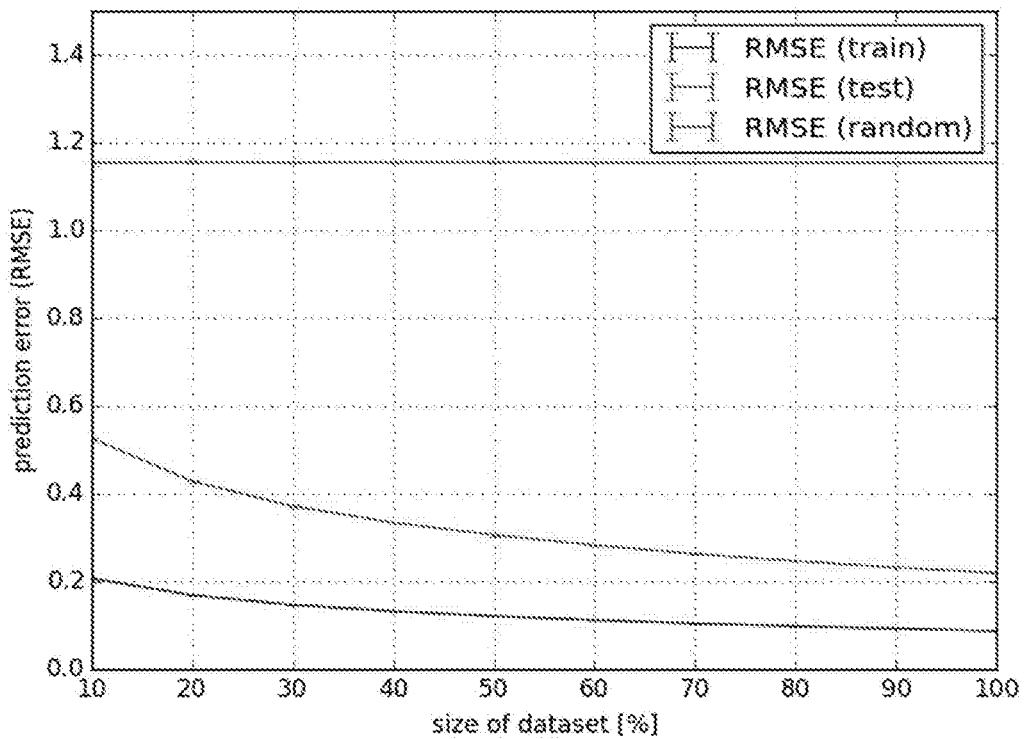
FIGS. 6 and 7 illustrate examples of the data validation processes on exemplary test data.

The above data validation process was tested against a clean dataset of wearable sensor data. This dataset includes 40 laps of racing data in 10 different practice runs which are composed of 1,655,102 data points. ⌞SEP⌟ evaluation uses the 5-fold cross validation method. Each segment is divided by laps and the prediction model is constructed using 10 different sizes of dataset from 10% to 100% for analytics experiment. The results of the EMG prediction are shown in FIG. 6. The best prediction error against the test dataset is about 0.220, while the error against the training data is 0.088 with 100% of the data. Note that the EMG data is scaled by standardization from the original data, meaning the mean equals 0 and the standard deviation equals 1.0. Therefore, this model results in approximately 22% error in the predicted EMG signal and this prediction outperforms a random prediction model as shown in FIG. 6. The prediction performance can be improved by further refinement of the machine learning model. Also, as FIG. 5 shows, the error gets smaller as the size of dataset increases.

Figure 7:
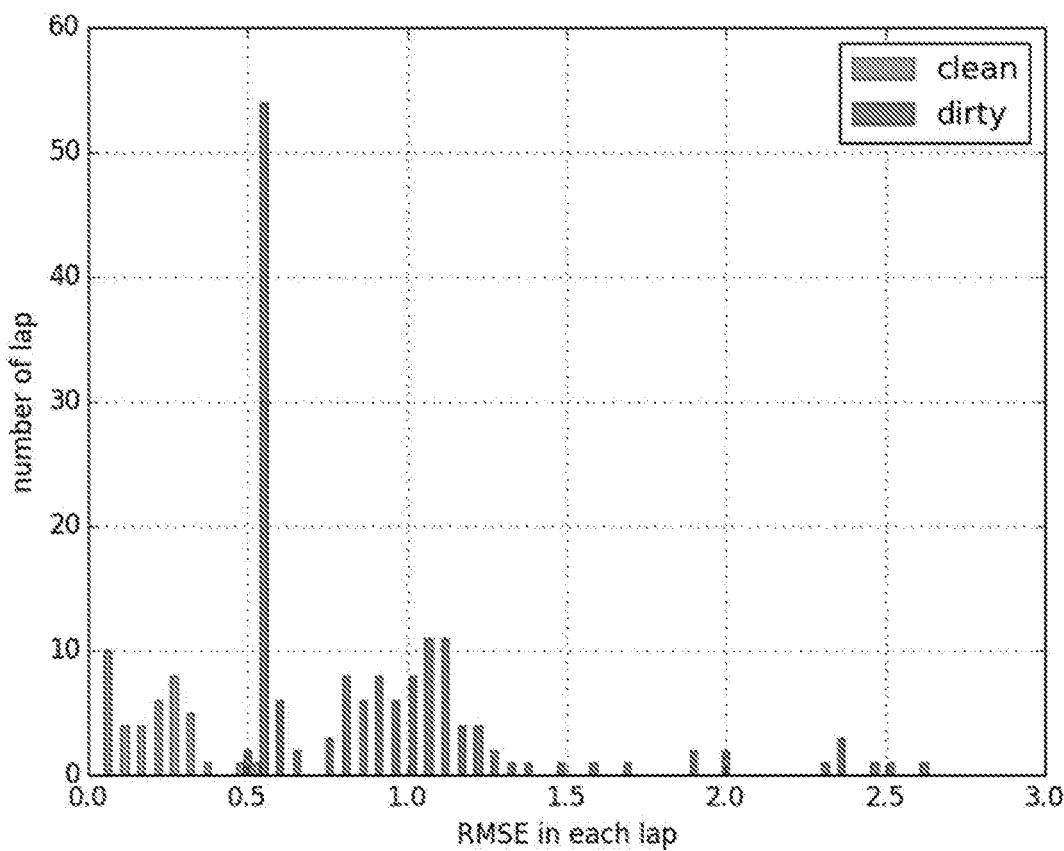

FIG. 7 shows the results of the quality validation and shows the histogram of RMSE for both clean and dirty classification. Note that this figure shows all results obtained by 5 repeated evaluation at once. The RMSE of the clean data is relatively small because the EMG prediction performs well for clean data. However, RMSE of dirty data varies widely and is relatively large since the predicted EMG value deviates from the actual EMG value. Because the car telemetry data is not likely to be affected by noise, the prediction should roughly perform within 22% error. Therefore, the actual EMG value is considered to have no abnormality.

If the classification threshold is set to be the minimum value of the RMSE of dirty data, 0.507 in this case, the accuracy of classification becomes 99.48%. Realistically, the threshold should be set up conservatively. Although this causes some loss from the clean dataset available for further analysis, including noisy data for further analytics could lead to faulty analysis, which is far worse than losing some valid data.

Actionable Insight Analytics

In one example, this actionable insights analysis may be performed by the insights analytics engine 304 as shown in FIG. 3. In the example of the racing care and forearm fatigue, the actionable insights may be potential points where the driver can improve performance. For example, the actionable insights may be locations on the race circuit in which the driver should be relaxing his forearms during the race to reduce forearm fatigue and therefore increase drive performance.

Figure 8:
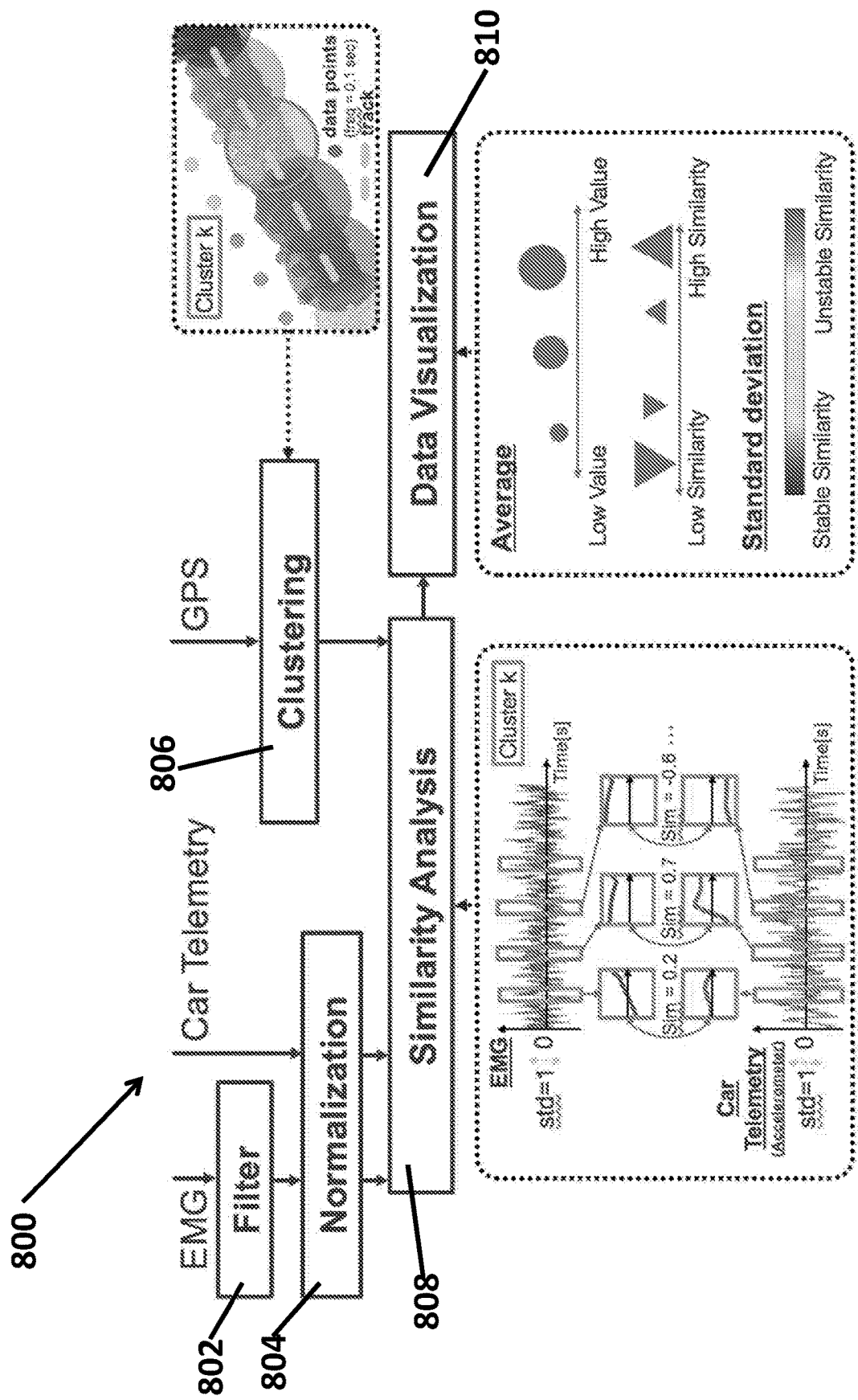
FIG. 8 illustrates an example of an insight analysis process that may be performed by the insights analytics engine of the racing analytics engine.

A process for actionable insights 800 (as shown in FIG. 8) may utilize unsupervised learning. In the example of using the system to improve driver performance insights for forearm fatigue, the process 800 may identify the EMG correlations with various data points from the car's telemetry information along various GPS coordinates along the race track. As shown in FIG. 8, the process may receive car telemetry data, GPS data and the EMG data. The process 800 may include a filter process 802 for filtering the EMG data to prevent the unreasonable or spiky noise, a normalization process 804 for normalizing the EMG data and the telemetry data, a clustering process 806 that uses the GPS data and performs, for example k-means clustering, on the GPS location data to aggregate the data from multiple laps in the same vicinity, a similarity process 808 that receives the filtered and normalized EMG data and the telemetry data and the clustered GPS data and determines the similarity between normalized EMG and car telemetry data is computed at each clustered location, and a data visualization process 810 that produces data visualization using an interactive tool (an example of which is shown in FIG. 8 (for the pipeline) and FIGS. 10-13 showing the interactive tool.)

Filtering Process

Figure 9:
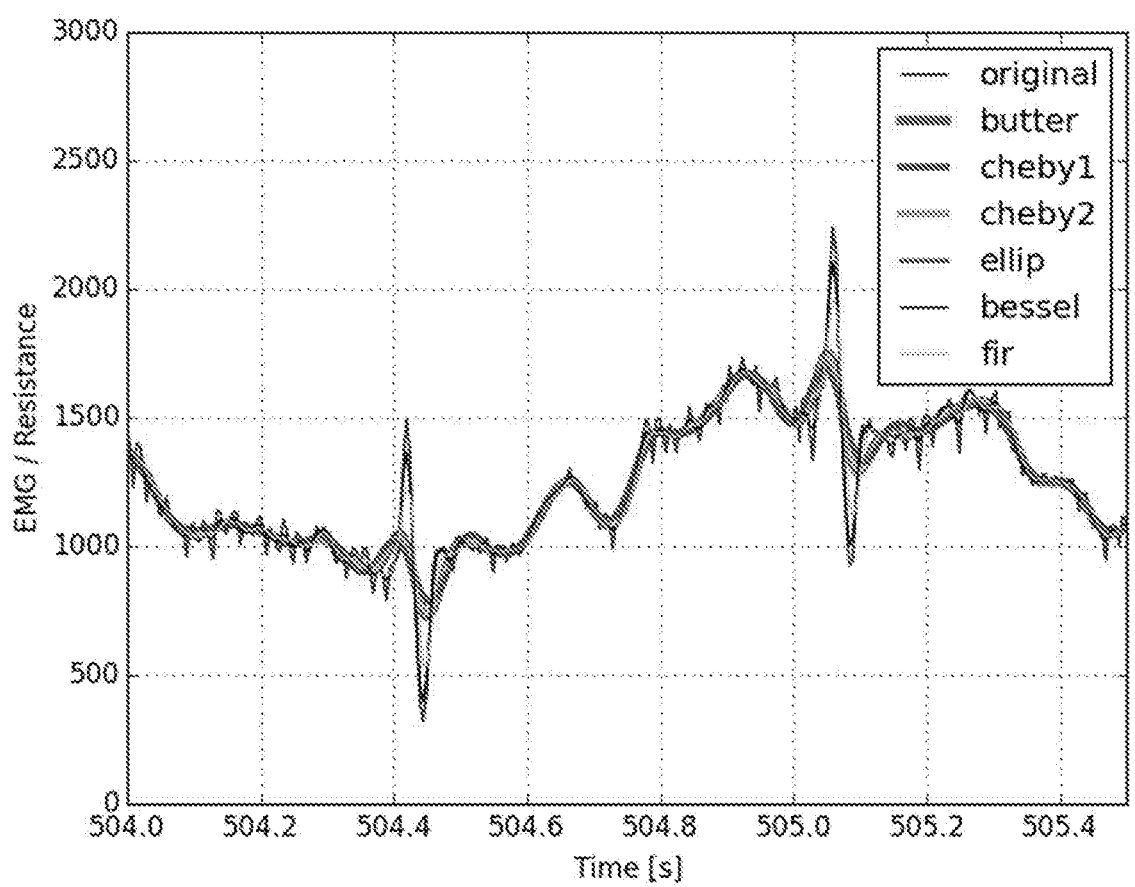
FIG. 9 shows the noisy wearable sensor data.

The filter process 802 may remove unreasonable or spiky noise from the wearable sensor data. As shown in FIG. 9, the original EMG signal has spiky noise within 0.1 seconds with the interval of about 0.7 seconds. This appears to be due to the sensor measuring the driver's pulse within the EMG data that may be removed. The filter process 802 may use a Chebyshev type2 filter. Other possible filters that may be used include Butterworth, Chebyshev type1, Elliptic, Bessel and/or FIR (hamming window).

Clustering Process

Figure 12:
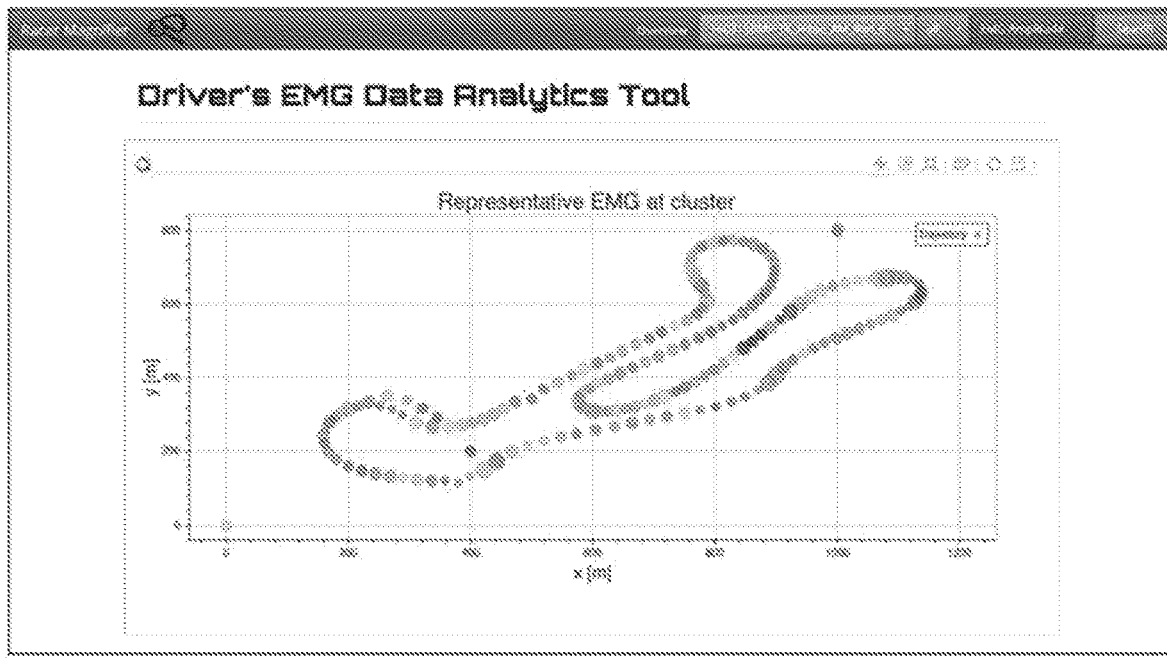

The inclusion of too many data points in time-series data makes it hard for users to intuitively understand a driver's behavior. The clustering process 806, such as k-means clustering in one example, allows the process to understand the general behavior at each GPS location by aggregating the locations on the track. The initial centroids for k-means clustering are determined based on the complete GPS data on track for one lap. For example, each centroid may be picked 0.5 second intervals. Since the sampling rate of GPS is 0.1 second, clustering aggregates approximately 5 data samples within one location. For example, the method lets $^l d^{(c,j)}$ denote the data point within 0.1 second, where l is the lap index, c is the cluster index, and j is the data index in cluster c. Through the clustering process 806, the cluster index c and data index j is determined, while l is given in raw data. This $^l d^{(c,j)}$ owns data of both EMG data and car telemetry data with one GPS data point. Note that this clustering only considers clean data. The classification above determines lap index l whose data meets quality levels for further clustering analysis and, if the data in lap l is classified as not clean, it is simply excluded. An example of the data resulting from the clustering for an exemplary race circuit is shown in FIG. 12.

Normalization Process

Before computing similarity, normalization and linear interpolation may be used, as heterogeneous data points have different scales and sampling rates. Thus, first, every data point is standardized, meaning the mean equals 0 and the standard deviation equals 1.0. Second, every data point is separated with the time interval of 0.1 seconds. Third, linear interpolation is applied to make the dataset comparable, because the sampling rate differs from sensor to sensor.

Similarity Process

The similarity process 808 may determine a similarity between EMG and car telemetry data that can be computed as follows $$sim_j^{[c]} = \frac{1}{1 + 4e_j^{[c]}}, \quad e_j^{[c]} = \frac{\sum_{i=0}^{N^{[c,j]}} |EMG_i^{[c,j]} - Telemetry_i^{[c,j]}|}{N^{[c,j]}}, \quad (2)$$

where $sim_j^{(c)}$ denotes the similarity between EMG and car telemetry data on j th data point in cluster c, $e_j^{(c)}$ denotes mean absolute error between EMG and telemetry data on n th data point in cluster c, $N^{(c,j)}$ denotes the number of sample points after linear interpolation, and $EMG_i^{(c,j)}$ and $Telemetry_i^{(c,j)}$ denote the i th sample points of j th data point in cluster c.

Based on multiple similarity scores in each cluster, the average and the standard deviation are computed as follows. These information is used for next step, data visualization.

$$ave^{[c]} = \frac{\sum_j sim_j^{[c]}}{N^{[c]}}, \quad std^{[c]} = \sqrt{\frac{1}{n}\sum_j (sim_j^{[c]} - ave^{[c]})^2} \quad (3)$$

Figure 15:
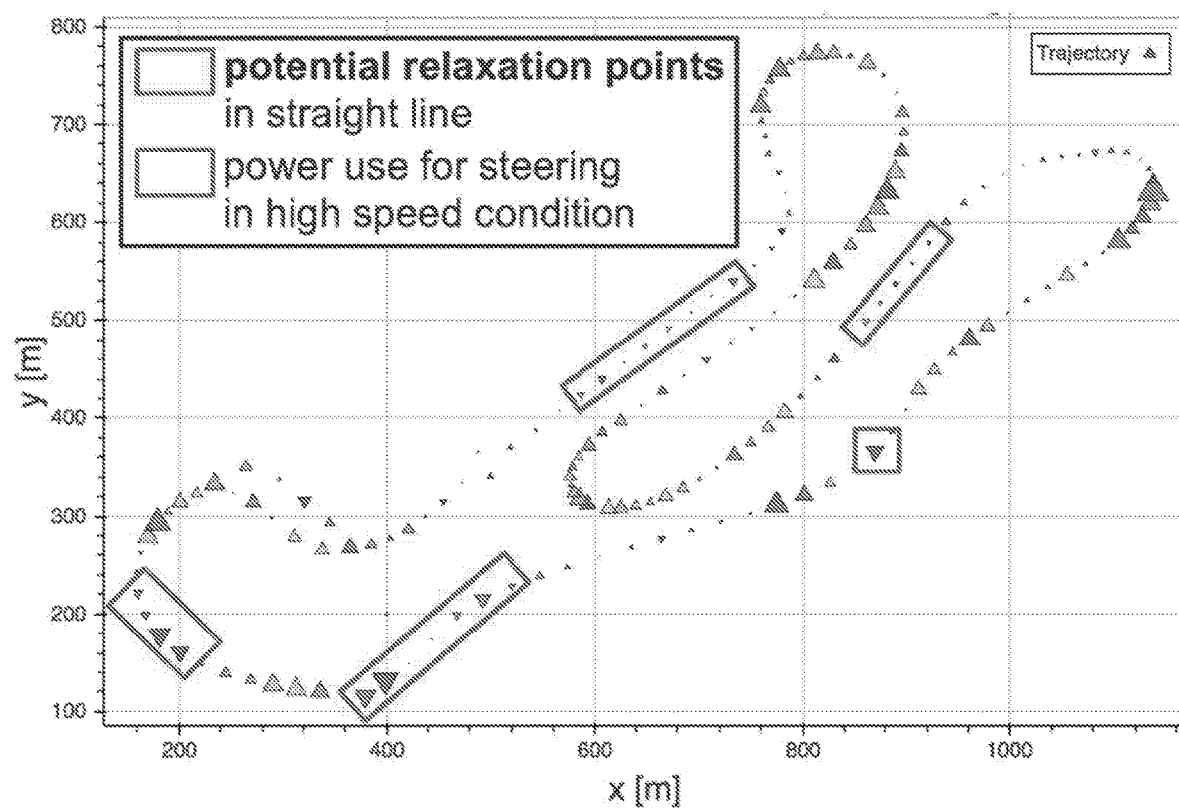
FIG. 15 illustrates an example of the data visualization for the similarity analysis.

An example of the resulting data from the above similarity analysis process for an exemplary race circuit is shown in FIG. 15. The example in FIG. 15 also shows actionable insights (potential relaxation points around the race circuit.

Visualization Process

Figure 10:
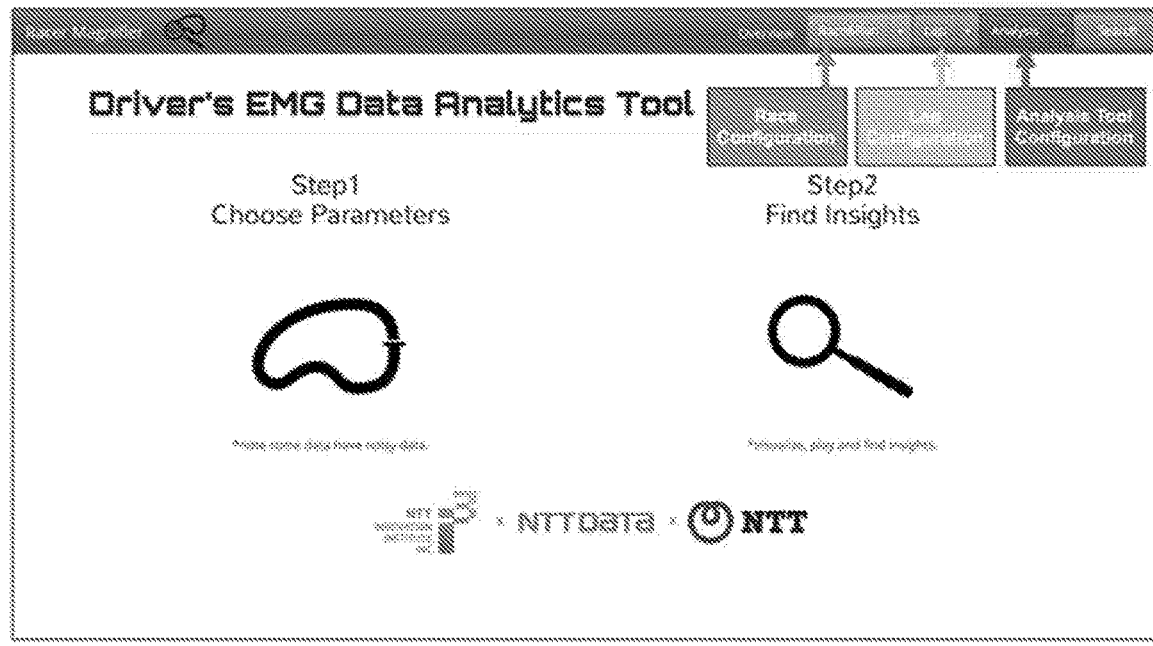
FIGS. 10-13 illustrate examples of the user interfaces generates by an example of a web based visualization tool.
Figure 11:
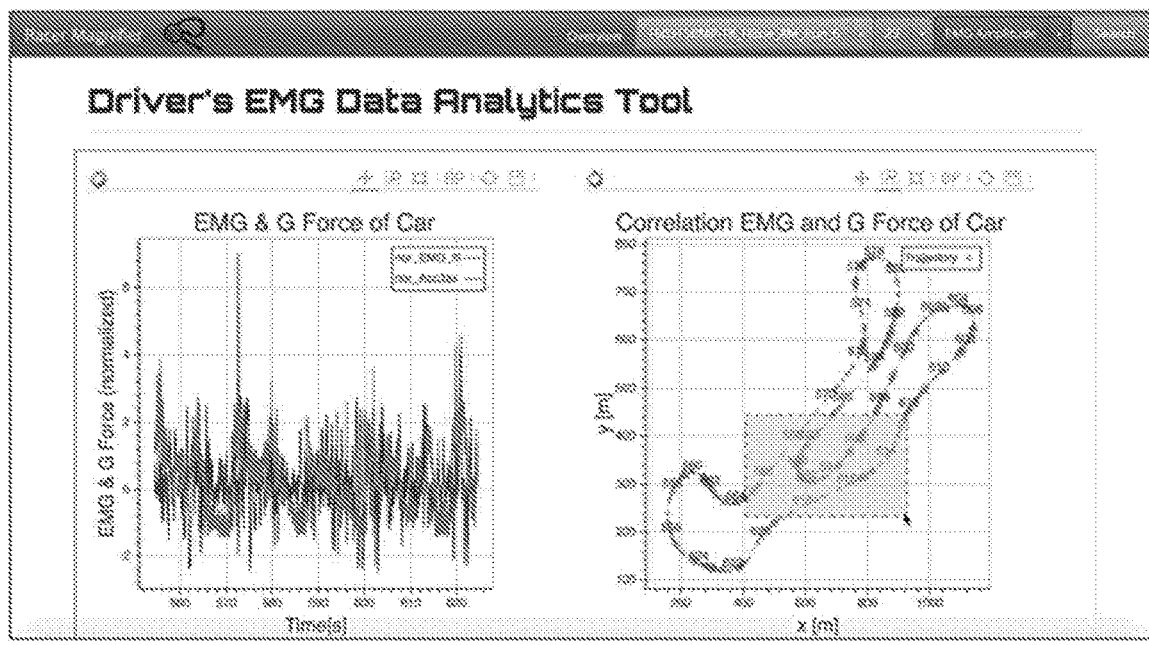
Figure 13:
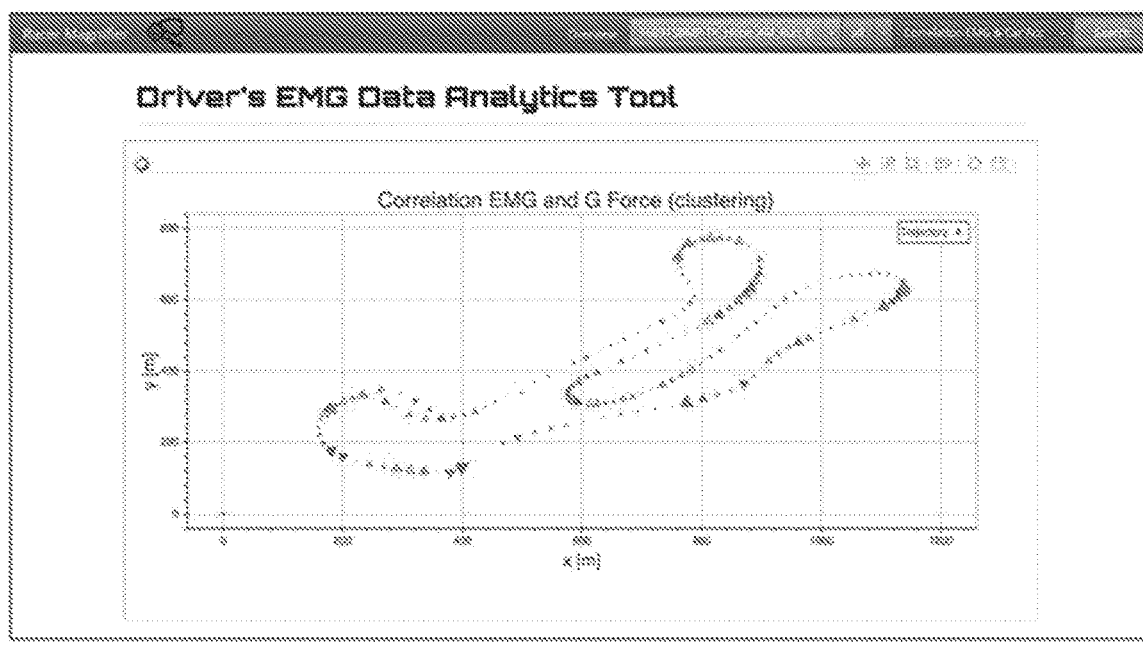
Figure 14:
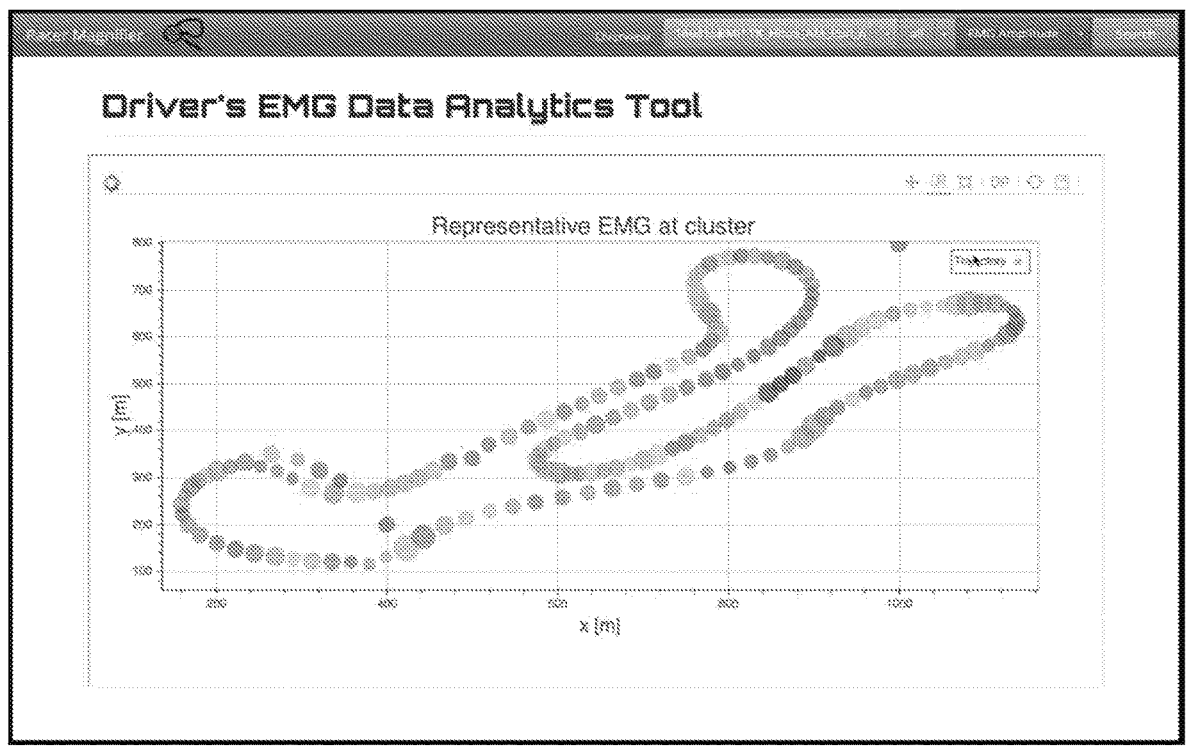
FIG. 14 illustrates an example of the data visualization for the clustering analysis.

It is important to provide the race team the ability to cultivate data and discover actionable feedback towards performance improvements themselves. The visualization process 810 may use a data visualization tool with a web-based user interface. This tool offers the ability to choose a parameter and instantly searching for an analytics result. FIG. 10 shows an initial screen. Using this tool, users can choose the parameters of race, lap and the data analytics tool to be used. Once users choose the parameters, the result is displayed as shown in FIG. 11. Here, users can PAN, zoom or perform other manipulation of the data. The examples of clustering analytics results are shown in FIG. 12 and FIG. 13. The meanings of the shapes and colors are described in FIG. 8 above.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the disclosure and its practical applications, to thereby enable others skilled in the art to best utilize the disclosure and various embodiments with various modifications as are suited to the particular use contemplated.

The system and method disclosed herein may be implemented via one or more components, systems, servers, appliances, other subcomponents, or distributed between such elements. When implemented as a system, such systems may include an/or involve, inter alia, components such as software modules, general-purpose CPU, RAM, etc. found in general-purpose computers. In implementations where the innovations reside on a server, such a server may include or involve components such as CPU, RAM, etc., such as those found in general-purpose computers.

Additionally, the system and method herein may be achieved via implementations with disparate or entirely different software, hardware and/or firmware components, beyond that set forth above. With regard to such other components (e.g., software, processing components, etc.) and/or computer-readable media associated with or embodying the present inventions, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the system and method may be achieved via or performed by logic and/or logic instructions including program modules, executed in association with such components or circuitry, for example. In general, program modules may include routines, programs, objects, components, data structures, etc. that perform particular tasks or implement particular instructions herein. The inventions may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, however no media of any such type herein includes transitory media. Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

While the foregoing has been with reference to a particular embodiment of the disclosure, it will be appreciated by those skilled in the art that changes in this embodiment may be made without departing from the principles and spirit of the disclosure, the scope of which is defined by the appended claims.

The invention claimed is:

1. A car data analytics method, comprising:
   generating, using a sensor attached to a driver of a vehicle, data about a forearm muscle of the driver during operation of the vehicle;

capturing, using a telemetry system located in the vehicle, the data about the forearm muscle of the driver and vehicle telemetry data during operation of the vehicle;
determining if the forearm muscle data is valid; and
processing the valid muscle sensor data and vehicle telemetry data to generate an actionable insight for the driver using the valid muscle sensor data and vehicle telemetry data.

2. The method of claim 1 further comprising comparing the received muscle sensor data to a set of predicted muscle data and determining that the muscle sensor data is valid if there is not a significant deviation between the received muscle sensor data and the set of predicted muscle data.

3. The method of claim 2 further comprising using machine learning to perform the comparison of the received muscle sensor data and the set of predicted muscle data.

4. The method of claim 1 further comprising filtering the received muscle data to process the valid muscle sensor data.

5. The method of claim 4 further comprising receiving muscle sensor data and vehicle telemetry data for multiple laps of the vehicle and clustering the muscle sensor data and vehicle telemetry data for multiple laps of the vehicle to aggregate the muscle sensor data and vehicle telemetry data for a particular vehicle location during each lap.

6. The method of claim 5 further comprising generating a similarity between muscle sensor data and vehicle telemetry data to generate the actionable insight for the driver.

7. The method of claim 1 further comprising generating data about a heart of the driver during operation of the driver.

8. A system for car data analytics, comprising:
a sensor attached to a driver of a vehicle that generates data about a forearm muscle of the driver during operation of the vehicle;
a telemetry system located in the vehicle that captures the data about the forearm muscle of the driver and captures vehicle telemetry data during operation of the vehicle;
a data analytics system having a processor, a memory and a plurality of lines of instructions that is configured to:
receive the muscle sensor data and the vehicle telemetry data;
determine if the muscle sensor data is valid;
process the valid muscle sensor data and vehicle telemetry data to generate an actionable insight for the driver using the valid muscle sensor data and vehicle telemetry data.

9. The system of claim 8, wherein the data analytics system is further configured to compare the received muscle sensor data to a set of predicted muscle data and determine that the muscle sensor data is valid if there is not a significant deviation between the received muscle sensor data and the set of predicted muscle data.

10. The system of claim 9, wherein the data analytics system is further configured to use machine learning to perform the comparison of the received muscle sensor data and the set of predicted muscle data.

11. The system of claim 8, wherein the data analytics system is further configured to filter the received muscle data to process the valid muscle sensor data.

12. The system of claim 11, wherein the data analytics system is further configured to receive muscle sensor data and vehicle telemetry data for multiple laps of the vehicle and cluster the muscle sensor data and vehicle telemetry data for multiple laps of the vehicle to aggregate the muscle sensor data and vehicle telemetry data for a particular vehicle location during each lap.

13. The system of claim 12, wherein the data analytics system is further configured to generate a similarity between muscle sensor data and vehicle telemetry data to generate the actionable insight for the driver.

14. The system of claim 8, wherein the sensor further comprises a wearable fabric.

15. The system of claim 14 further comprising a sensor that generates data about a heart of the driver during operation of the vehicle.

16. The system of claim 8, wherein the telemetry system captures the muscle sensor data wirelessly.

17. The system of claim 8, wherein the vehicle telemetry data further comprises one or more of accelerometer data, steering angle data, speed data, throttle data and brake pressure data.

* * * * *